US008888858B2

(12) United States Patent
Brown et al.

(10) Patent No.: US 8,888,858 B2
(45) Date of Patent: Nov. 18, 2014

(54) FEMORAL TROCHLEA PROSTHESES

(75) Inventors: Jeffrey D. Brown, Warsaw, IN (US); Adam M. Griner, Columbia City, IN (US); Robert A. Hodorek, Warsaw, IN (US); Raymond C. Parisi, Wakarusa, IN (US); Brian E. Vanskyock, Fort Wayne, IN (US); Justin J. May, Leesburg, IN (US); James C. Harris, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 32 days.

(21) Appl. No.: 12/506,356

(22) Filed: Jul. 21, 2009

(65) Prior Publication Data

US 2009/0281583 A1 Nov. 12, 2009

Related U.S. Application Data

(63) Continuation of application No. 11/671,643, filed on Feb. 6, 2007, now Pat. No. 7,582,118.

(51) Int. Cl.
*A61F 2/38* (2006.01)
*A61F 2/30* (2006.01)

(52) U.S. Cl.
CPC ..... *A61F 2/3877* (2013.01); *A61F 2002/30892* (2013.01); *A61F 2002/3092* (2013.01); *A61F 2/30767* (2013.01); *A61F 2002/30909* (2013.01); *A61F 2002/30878* (2013.01)
USPC ...................... 623/20.36; 623/20.17; 623/20.3

(58) Field of Classification Search
CPC ........................................................ A61F 2/38
USPC ............ 623/20.14, 20.15, 20.18, 20.19, 20.3, 623/20.35, 20.36, 14.12, 16.11, 18.11, 623/19.13, 20.11, 21.18, 21.11, 21.12; 606/88
See application file for complete search history.

(56) References Cited

U.S. PATENT DOCUMENTS

| 4,344,192 | A | 8/1982 | Imbert |
| 5,336,266 | A | 8/1994 | Caspari et al. |
| 5,645,602 | A | 7/1997 | Albrektsson et al. |
| 5,702,459 | A | 12/1997 | Hummer et al. |

(Continued)

FOREIGN PATENT DOCUMENTS

| CA | 2601484 A1 | 8/2008 |
| EP | 1955676 B1 | 3/2011 |

(Continued)

OTHER PUBLICATIONS

EP search report mailed May 5, 2008 in related EP application EP08250441.6.

(Continued)

*Primary Examiner* — Yashita Sharma
(74) *Attorney, Agent, or Firm* — Schwegman Lundberg & Woessner, P.A.

(57) ABSTRACT

Various embodiments of femoral trochlea prostheses useable in a knee joint. The knee joint includes a patella and a distal femur with a femoral trochlea, or patello-femoral groove. In one embodiment, a femoral trochlea prosthesis includes a distal tail. In another embodiment, a femoral trochlea prosthesis includes a wing or extension portion. In yet another embodiment, a set of femoral trochlea prostheses includes a plurality of prostheses having differing thicknesses. In still another embodiment, a femoral trochlea prosthesis includes a porous medium on various portions of the prosthesis.

10 Claims, 3 Drawing Sheets

(56) References Cited

U.S. PATENT DOCUMENTS

| | | | |
|---|---|---|---|
| 5,824,098 A | 10/1998 | Stein | |
| 5,879,354 A | 3/1999 | Haines et al. | |
| 6,190,415 B1 | 2/2001 | Cooke et al. | |
| 6,416,552 B1 | 7/2002 | Hoeppner et al. | |
| 6,494,914 B2* | 12/2002 | Brown et al. | 623/20.3 |
| 6,616,696 B1 | 9/2003 | Merchant | |
| 6,679,917 B2* | 1/2004 | Ek | 623/20.14 |
| 6,797,006 B2* | 9/2004 | Hodorek | 623/20.36 |
| 7,172,597 B2 | 2/2007 | Sanford | |
| 7,258,701 B2 | 8/2007 | Aram et al. | |
| 7,582,118 B2 | 9/2009 | Brown et al. | |
| 7,963,969 B2 | 6/2011 | Sanford | |
| 8,128,704 B2 | 3/2012 | Brown et al. | |
| 2003/0120346 A1 | 6/2003 | Mercinek et al. | |
| 2003/0181984 A1 | 9/2003 | Abendschein | |
| 2003/0236521 A1* | 12/2003 | Brown et al. | 606/80 |
| 2004/0236428 A1 | 11/2004 | Burkinshaw et al. | |
| 2005/0143833 A1* | 6/2005 | Merchant | 623/20.31 |
| 2005/0154471 A1 | 7/2005 | Aram et al. | |
| 2006/0122616 A1 | 6/2006 | Bennett et al. | |
| 2007/0123992 A1 | 5/2007 | Sanford | |
| 2007/0299528 A9 | 12/2007 | Lotke | |
| 2008/0188855 A1 | 8/2008 | Brown et al. | |
| 2008/0188942 A1 | 8/2008 | Brown et al. | |
| 2012/0116525 A1 | 5/2012 | Brown | |

FOREIGN PATENT DOCUMENTS

| | | | |
|---|---|---|---|
| FR | 2521421 A1 | | 8/1983 |
| FR | 2594323 A1 | | 8/1987 |
| FR | 2676641 A1 * | | 11/1992 |
| FR | 2682589 A1 | | 4/1993 |
| FR | 2740325 A1 | | 4/1997 |
| WO | WO03/068119 A2 | | 8/2003 |

OTHER PUBLICATIONS

EP search report mailed May 27, 2008 in EP application EP08250442.4.
Product Overview, Knee Systems, Avon Femoral Component, Stryker Orthopaedics, accessed Nov. 13, 2006.
Product Brochure, Link Knee Orthplasty Implants, accessed Nov. 13, 2006.
Product Brochure, Kinamed Incorporated, KineMatch Patello-Femoral Replacement, accessed Nov. 13, 2006, Copyright 2006.
Product Brochure, Ceraver Patello-Femoral Prosthesis, Unicompartimental prosthesis, accessed Nov. 13, 2006.
Surgical Technique, Johnson & Johnson LCS PFJ, accessed Nov. 13, 2006, Copyright 2000-2006.
Surgical Technique, Vanguard Patello Femoral Replacement System, Biomet Orthopedics, Inc., Copyright 2004.
Surgical Technique, Natural-Knee II Patello-Femoral Joint System, Zimmer, Copyright 2004.
Product Brochure, Natural-Knee II Patello-Femoral Joint System, Zimmer, Copyright 2005.
Surgical Technique, Avon Patello-Femoral Arthroplasty, Stryker Howmedica Osteonics, Aug. 2003.
U.S. Appl. No. 11/671,645, Preliminary Amendment filed Oct. 6, 2011, 5 pgs.
U.S. Appl. No. 13/355,168, Final Office Action mailed May 16, 2013, 10 pgs.
U.S. Appl. No. 13/355,168, Preliminary Amendment filed Jan. 20, 2012, 5 pgs.
U.S. Appl. No. 13/355,168, Response filed Feb. 25, 2013 to Non Final Office Action mailed Nov. 23, 2012, 9 pgs.
U.S. Appl. No. 13/355,168, Response filed Sep. 17, 2012 to Restriction Requirement mailed Jul. 18, 2012, 5 pgs.
European Application Serial No. 08250441.6, Response filed Feb. 18, 2009 to Search Report mailed May 27, 2008, 15 pgs.
European Application Serial No. 08250441.6, Search Report mailed May 27, 2008, 6 pgs.
European Application Serial No. 08250442.4, Search Report mailed May 27, 2008, 5 pgs.
U.S. Appl. No. 11/671,645, Examiner Interview Summary mailed Apr. 4, 2011, 4 pgs.
U.S. Appl. No. 11/671,645, Response filed Apr. 21, 2011 to Final Office Action mailed Jan. 11, 2011, 8 pgs.
U.S. Appl. No. 13/355,168, Non Final Office Action mailed Jan. 17, 2014, 8 pgs.
U.S. Appl. No. 13/355,168, Response filed Nov. 15, 2013 to Final Office Action mailed May 16, 2013, 12 pgs.
Canadian Application Serial No. 2,601,484, Office Action mailed Jan. 15, 2013, 3 pgs.
U.S. Appl. No. 13/355,168, Response filed Apr. 17, 2014 to Non-Final Office Action mailed Jan. 17, 2014, 9 pgs.
Canadian Application Serial No. 2,602,262, Office Action mailed Jan. 21, 2014, 2 pgs.
Canadian Application Serial No. 2,601,484, Response filed May 14, 2014 to Office Action mailed Nov. 15, 2013, 11 pgs.
European Application Serial No. 08250442.4, Office Action mailed Feb. 20, 2009, 1 pg.
European Application Serial No. 08250442.4, Response filed Aug. 26, 2009 to Office Action mailed Feb. 20, 2009, 9 pgs.
U.S. Appl. No. 11/671,643, Non Final Office Action mailed Aug. 27, 2008, 9 pgs.
U.S. Appl. No. 11/671,643, Notice of Allowance mailed Apr. 23, 2009, 9 pgs.
U.S. Appl. No. 11/671,643, Response filed Jan. 27, 2009 to Non Final Office Action mailed Aug. 27, 2008, 7 pgs.
U.S. Appl. No. 11/671,643, Response filed Aug. 11, 2008 to Restriction Requirement mailed Jul. 22, 2008, 2 pgs.
U.S. Appl. No. 11/671,643, Restriction Requirement mailed Jul. 22, 2008, 8 pgs.
U.S. Appl. No. 11/671,645, Final Office Action mailed Jan. 11, 2011, 11 pgs.
U.S. Appl. No. 11/671,645, Non Final Office Action mailed Jan. 7, 2010, 10 pgs.
U.S. Appl. No. 11/671,645, Non Final Office Action mailed Jul. 7, 2010, 11 pgs.
U.S. Appl. No. 11/671,645, Notice of Allowance mailed Jul. 6, 2011, 7 pgs.
U.S. Appl. No. 11/671,645, Notice of Allowance mailed Oct. 20, 2011, 5 pgs.
U.S. Appl. No. 11/671,645, Response filed Apr. 7, 2010 to Non Final Office Action mailed Jan. 7, 2010, 7 pgs.
U.S. Appl. No. 11/671,645, Response filed Nov. 5, 2009 to Restriction Requirement mailed Oct. 8, 2009, 9 pgs.
U.S. Appl. No. 11/671,645, Response filed Nov. 8, 2010 to Non Final Office Action mailed Jul. 7, 2010, 10 pages.
U.S. Appl. No. 11/671,645, Restriction Requirement mailed Oct. 8, 2009, 9 pgs.
U.S. Appl. No. 13/355,168, Non Final Office Action mailed Nov. 23, 2012, 7 pgs.
U.S. Appl. No. 13/355,168, Restriction Requirement mailed Jul. 18, 2012, 6 pgs.

* cited by examiner

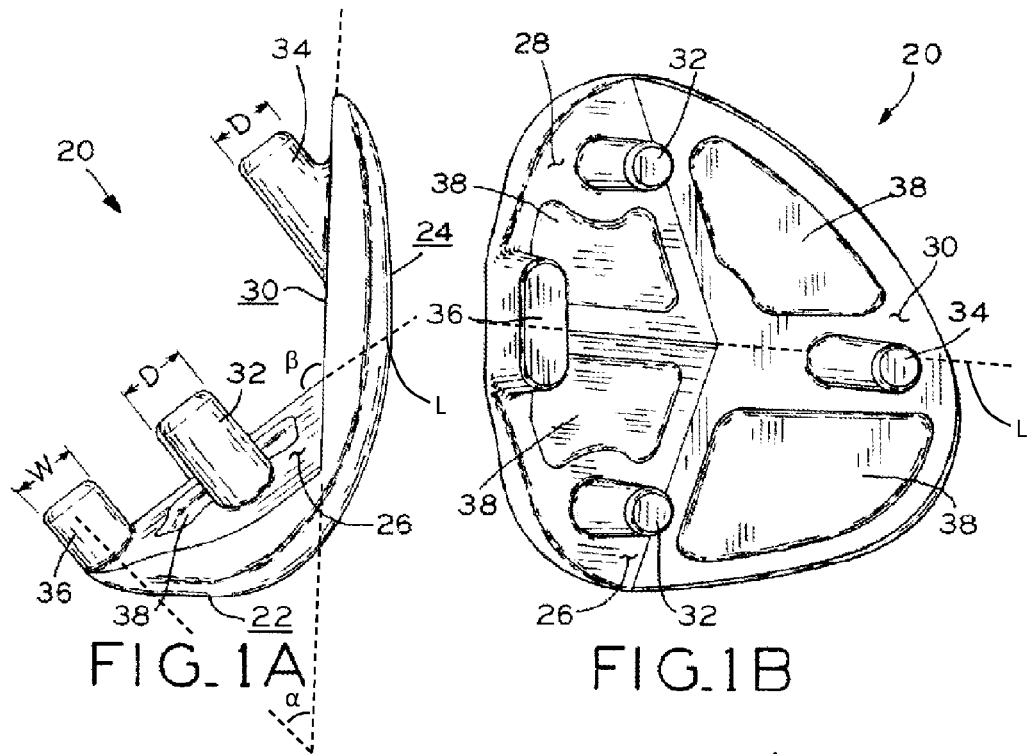
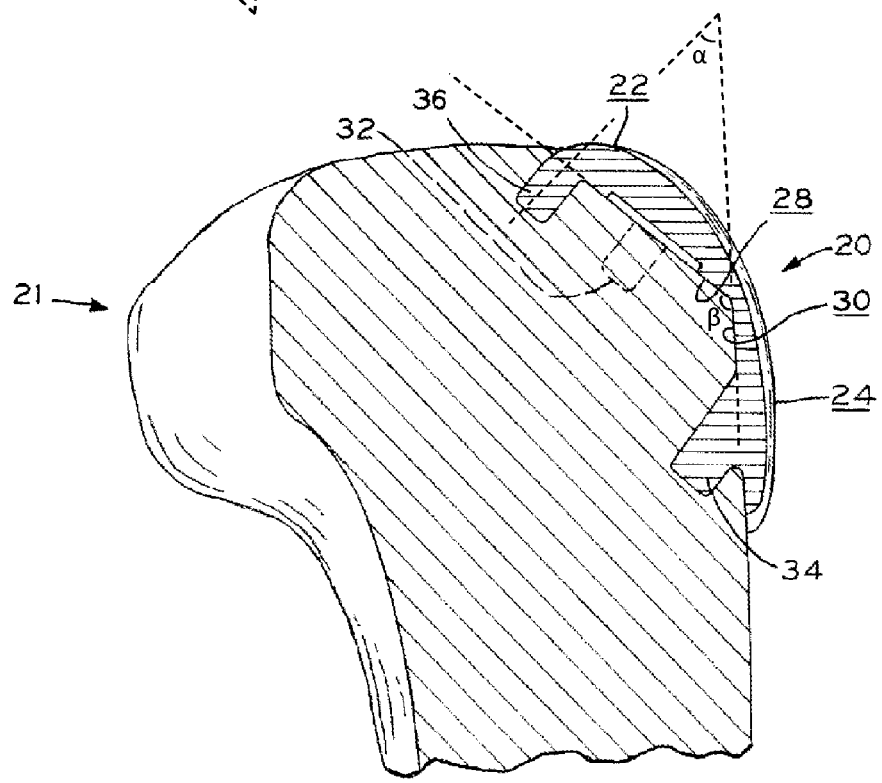
FIG. 1A  FIG. 1B
FIG. 1C

FEMORAL TROCHLEA PROSTHESES

CROSS-REFERENCE TO RELATED APPLICATIONS

This application is a continuation of co-pending U.S. patent application Ser. No. 11/671,643, filed Feb. 6, 2007, entitled FEMORAL TROCHLEA PROSTHESES, and assigned to the assignee of the present application, the disclosure of which is hereby expressly incorporated herein by reference.

BACKGROUND

1. Field of the Invention

The present invention relates to knee joint prostheses. More particularly, the present invention relates to various embodiments of exemplary femoral trochlea prostheses.

2. Description of the Related Art

Disease and trauma affecting the patello-femoral joint of a knee are commonly treated by surgically replacing the femoral trochlea with femoral trochlea implants or prostheses according to a procedure known as a patello-femoral joint (PFJ) replacement. Although femoral trochlea prostheses are provided in a range of varying sizes and are selected by surgeons to best fit the anatomy of a particular patient, improvements in the design of femoral trochlea prostheses are desired.

SUMMARY

The present disclosure provides various embodiments of femoral trochlea prostheses useable in a knee joint. The knee joint includes a patella and a distal femur with a femoral trochlea, or patello-femoral groove. In one embodiment, a femoral trochlea prosthesis includes a distal tail. In another embodiment, a femoral trochlea prosthesis includes a wing or extension portion. In yet another embodiment, a set of femoral trochlea prostheses includes a plurality of prostheses having differing thicknesses. In still another embodiment, a femoral trochlea prosthesis includes a porous medium on various portions of the prosthesis.

In one form thereof, the present disclosure provides a method of surgically repairing a distal femur of a knee joint. The method includes the steps of providing a femoral trochlea prosthesis including an articulating surface having a posterior-most end, a nonarticulating surface opposite the articulating surface, and at least one fixation support that projects from the nonarticulating surface, the posterior-most end of the articulating surface transitioning smoothly into the fixation support; positioning the nonarticulating surface of the prosthesis against the distal femur; and implanting the fixation support of the prosthesis into the distal femur such that posterior-most end of the articulating surface of the prosthesis transitions smoothly into the distal femur.

In another form thereof, the present disclosure provides a method of surgically repairing a distal femur of a knee joint. The method includes the steps of providing a femoral trochlea prosthesis including an articulating surface having a posterior-most end, a nonarticulating surface opposite the articulating surface, at least one fixation support that projects from the nonarticulating surface, and an arcuate transition surface that spans the posterior-most end of the articulating surface and the fixation support; resecting a portion of the distal femur to provide a resected surface; positioning the nonarticulating surface of the prosthesis against the resected surface of the distal femur; and implanting the fixation support of the prosthesis into the distal femur beyond the resected surface.

In yet another form thereof, the present disclosure provides a method of surgically repairing a distal femur of a knee joint. The method includes the steps of providing a femoral trochlea prosthesis including an anterior portion and a distal portion that extends obtusely relative to the anterior portion, the distal portion including a posterior-most end and at least one fixation support that extends from the posterior-most end acutely relative to the anterior portion; resecting the distal femur to provide a resected anterior surface and a resected distal surface; positioning the anterior portion of the prosthesis against the resected anterior surface of the distal femur and the distal portion of the prosthesis against the resected distal surface of the distal femur; and implanting the fixation support of the prosthesis into the distal femur beyond the resected distal surface.

BRIEF DESCRIPTION OF THE DRAWINGS

The above-mentioned and other features of this disclosure, and the manner of attaining them, will become more apparent and will be better understood by reference to the following description of embodiments of the disclosure taken in conjunction with the accompanying drawings, wherein:

FIG. 1A is a side view of an exemplary femoral trochlea prosthesis according to one embodiment of the present disclosure;

FIG. 1B is a backside or nonarticulating side view of the prosthesis of FIG. 1A;

FIG. 1C is a cross-sectional view of the prosthesis of FIG. 1A, further illustrating a portion of a distal femur in which the prosthesis is implanted;

Corresponding reference characters indicate corresponding parts throughout the several views. The exemplifications set out herein illustrate embodiments of the disclosure and such exemplifications are not to be construed as limiting the scope of the invention in any manner.

DETAILED DESCRIPTION

Figure 2:
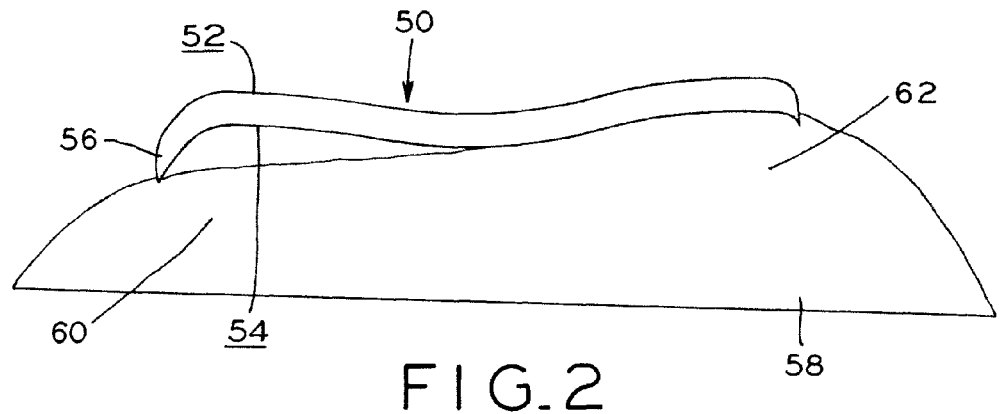
FIG. 2 is a proximal view of an exemplary femoral trochlea prosthesis according to another embodiment of the present disclosure.

The present disclosure provides various embodiments of femoral trochlea prostheses useable in a knee joint. The prostheses described herein may be useable in a knee joint in which a patella is resurfaced or a knee joint in which a patella is not resurfaced. The prostheses described herein may be secured to a femur with cement or, alternatively, without cement, such as with fixation pegs, a porous medium such as a material made using Trabecular Metal™ technology or Cancellous-Structured Titanium™ (CSTi™) technology, both available from Zimmer, Inc. of Warsaw, Ind., screws and/or cables, for example. The prostheses described herein may be formed of metal, polymer, or hydrogel. Moreover, due to the relatively small thicknesses of the prostheses described herein, the prostheses do not violate a primary total knee arthroplasty (TKA) envelope, i.e., minor or no adjustments of the primary TKA technique are required to revise a failed patello-femoral joint to a TKA.

All of the prostheses described herein may incorporate various features and be useable in systems using the techniques and methods described in U.S. patent application Ser. No. 11/671,645, filed on Feb. 6, 2007, now issued as U.S. Pat. No. 8,128,704, entitled FEMORAL TROCHLEA PROSTHESES, (hereinafter the "Co-pending Application"), and assigned to the assignee of the present application, the disclosure of which is expressly incorporated herein by reference.

Referring to FIGS. 1A, 1B, and 1C, femoral trochlea prosthesis 20 may include distal articulating surface 22, anterior articulating surface 24, and a plurality of nonarticulating surfaces. First distal nonarticulating surface 26, second distal nonarticulating surface 28, and anterior nonarticulating surface 30 are positionable against a resected patello-femoral joint, or femoral trochlea, of femur 21. In the illustrated embodiment of FIGS. 1A and 1B, distal nonarticulating surfaces 26 and 28 intersect along line L, which extends anteriorly/posteriorly across prosthesis 20. Articulating surfaces 22 and 24 may articulate against a resurfaced or unresurfaced patella (not shown). In an exemplary embodiment, as shown in FIG. 1C, distal articulating surface 22 may be shaped such that a sagittal profile of prosthesis 20 substantially matches the anatomy of femur 21. Due to the inlayed nature of prosthesis 20, a smooth transition between cartilage and prosthesis 20 is provided to facilitate a smooth articulation with the patella.

Prosthesis 20 may include a plurality of pegs to facilitate securement in femur 21 and support of prosthesis 20. Anterior bone peg 34 may extend from anterior nonarticulating surface 30. Distal bone pegs 32 may extend from distal nonarticulating surfaces 26 and 28.

Prosthesis 20 may also include distal tail 36 extending from distal nonarticulating surfaces 26 and 28. Distal tail 36 may be positioned at a point located most posteriorly on prosthesis 20 and may medially/laterally extend across at least a portion of distal nonarticulating surfaces 26 and 28. As shown in the illustrated embodiment of FIG. 1B, line L between distal nonarticulating surfaces 26 and 28 intersects distal tail 36, such that a sgittal plane extending anteriorly/posteriorly along line L to divide prosthesis 20 medially/laterally also intersects distal tail 36. Distal tail 36 extends a sufficient distance from surfaces 26 and 28 such that, when implanted in femur 21, distal tail 36 may provide additional fixation support between prosthesis 20 and femur 21. Furthermore, distal tail 36 may provide additional support for the patella in flexion and protects against a non-smooth, patella transition from flexion to extension, e.g., distal tail 36 facilitates prevention of patella catching. Prevention of patella catching facilitates use of prosthesis 20 in a variety of different anatomies. Distal tail 36 also may facilitate strengthening and/or stiffening of prosthesis 20, particularly in a region of prosthesis 20 experiencing high patellar loads, thereby enhancing the longevity of prosthesis 20. Moreover, distal tail 36 facilitates prevention of liftoff micromotion of prosthesis 20 because of the abutting relationship between distal tail 36 and femur 21.

In an exemplary embodiment, distal tail 36 extends substantially perpendicular, i.e., approximately at an angle of 90°, to distal nonarticulating surfaces 26 and 28, as shown in FIG. 1A. Distal tail 36 may extend at an angle to distal nonarticulating surfaces 26 and 28 as small as approximately 65°, 75°, or 85°, or as large as approximately 95°, 105°, or 115°. Because distal nonarticulating surfaces 26 and 28 form an obtuse angle β with anterior nonarticulating surface 30, as shown in FIGS. 1A and 1C, distal tail 36 (which extends substantially perpendicular to distal nonarticulating surfaces 26 and 28 as discussed above) extends acutely relative to anterior nonarticulating surface 30 at acute angle α. Distal bone pegs 32 and anterior bone peg 34 may also extend in directions substantially parallel to each other and to the extension direction of distal tail 36 to facilitate bone preparation and insertion of prosthesis 20. In an exemplary embodiment, distal tail 36 has width W which is substantially equal to diameter D of bone pegs 32 and 34. In this manner, a drill used to prepare femur 21 to receive bone pegs 32 and 34 may also be used to prepare femur 21 to receive distal tail 36. For example, the drill may first drill holes in femur 21 for receipt of bone pegs 32 and 34 and then drill a plurality of holes in femur 21 in a side-by-side manner to form a cavity for receipt of distal tail 36. The drill could alternatively be used in a router-type manner to form a cavity for receipt of distal tail 36. Such use of the same drill to form cavities in femur 21 for receipt of bone pegs 32, 34 and distal tail 36 facilitates a surgical procedure and eliminates the need for an additional surgical instrument used to form the cavity for distal tail 36. However, diameter D of bone pegs 32, 34 and width W of distal tail 36 may also be different values. In one embodiment, bone pegs 32, 34 and distal tail 36 extend an equal distance above their respective nonarticulating surfaces of prosthesis 20 to further facilitate bone preparation for receipt of prosthesis 20. In another embodiment, bone pegs 32, 34 and distal tail 36 extend unequally with respect to each other above their respective surfaces of prosthesis 20.

At least one of nonarticulating surfaces 26, 28, and 30 may include pockets or depressions 38 formed therein. Pockets 38 may receive cement to facilitate initial fixation of prosthesis 20 or allow for placement of porous materials therein to facilitate osseointegration of bone or cartilage into prosthesis 20. Pockets 38 advantageously are configured to contain cement or porous material placed therein, thereby enhancing fixation and fatigue resistance of prosthesis 20. Pockets 38 may be self-contained, i.e., surfaces 26, 28, or 30 act as rails or walls to substantially surround pockets 38 such that any material placed in pockets 38 is maintained in pockets 38 when prosthesis 20 is secured to femur 21.

Referring now to FIG. 2, femoral trochlea prosthesis 50 is conceptually shown and may be implantable on distal femur 58. In a dysplastic condition as shown in FIG. 2, distal femur 58 may have less bone on medial condyle 60 as compared to lateral condyle 62, or vice versa. To accommodate such a dysplastic condition, prosthesis 50 may be used. Prosthesis 50 may include articulating surface 52 which may have an asymmetric patella groove angle. Prosthesis 50 may also include nonarticulating surface 54 including some flat surfaces and/or some contoured surfaces. In an exemplary embodiment, prosthesis 50 includes wing or extension 56. Wing 56 may be disposed on a side of prosthesis 50 to match the dysplastic condition of distal femur 58. For example, as shown in FIG. 2, wing 56 is disposed as a projecting portion on the medial side of prosthesis 50 to compensate for the dysplastic condition of medial condyle 60. The projecting portion of prosthesis 50 defined by wing 56 forces the medial condyle of prosthesis 50 anteriorly away from femur 58 to more closely replicate a normal anatomical condition. Wing 56 may define a pocket between prosthesis 50 and distal femur 58 to facilitate containment of cement or porous material disposed between nonarticulating surface 52 and distal femur 58. Wing 56 extends from nonarticulating surface 52 of prosthesis 50 to physically contact medial condyle 60, thereby enhancing support for prosthesis 50 when used with a dysplastic femur 58. Advantageously, prosthesis 50 may account for variable femoral anatomy while facilitating minimal or no bone resection prior to implantation and ensuring good fixation and support of prosthesis 50 in distal femur 58. When prosthesis 50 is implanted, wing 56 of prosthesis 50 advantageously contacts distal femur 58, thereby providing a pocket for containing cement and porous material disposed between nonarticulating surface 52 and femur 58 as well as reducing the potential of soft tissue impingement on the edge of prosthesis 50. In another embodiment, wing 56 may extend around the entire perimeter defined by nonarticulating surface 52 of prosthesis 50. In an exemplary embodiment, wing 56 may be confined to certain desired locations on prosthesis 50.

Figure 3A:
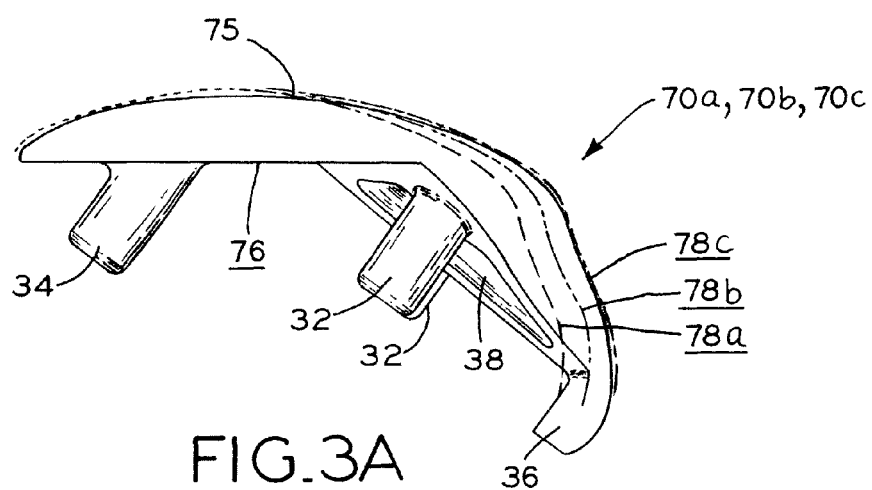
FIG. 3A is a side view of exemplary femoral trochlea prostheses according to yet another embodiment of the present disclosure.
Figure 3B:
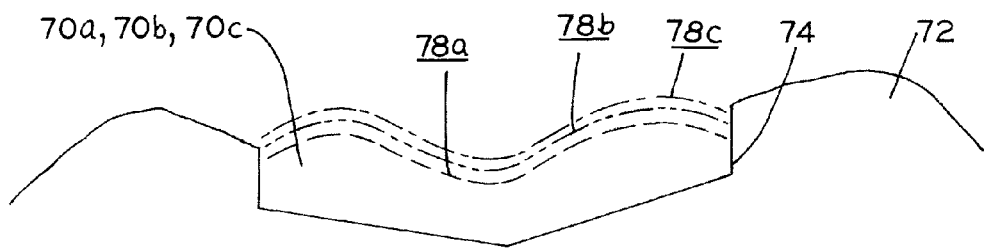
FIG. 3B is a proximal view of a portion of a distal femur with the various prostheses of FIG. 3A implanted therein.

Referring now to FIGS. 3A and 3B, a set of prostheses including femoral trochlea prostheses 70a, 70b, and 70c each may include anterior articulating surface 75, anterior nonarticulating surface 76, a plurality of bone or fixation pegs 32, 34, distal tail 36, and pockets 38, as described above with reference to FIGS. 1A, 1B, and 1C. Prosthesis 70a includes distal articulating surface 78a, prosthesis 70b includes distal articulating surface 78b, and prosthesis 70c includes distal articulating surface 78c. As shown in FIGS. 3A and 3B, articulating surfaces 78a, 78b, and 78c define three different thicknesses of distal articulating surface 78 of each prosthesis 70, for example. Although the set of prostheses is shown as including only three prostheses 70a, 70b, 70c, more prostheses 70 may be provided in the set of prostheses. Each prosthesis 70a, 70b, and 70c is implantable in resected portion 74 of distal femur 72, as shown in FIG. 3B. Advantageously, the set of prostheses 70 defined by prostheses 70a, 70b, and 70c provide a plurality of choices for thickness of distal articulating surface 78 once resected portion 74 has been completed. The surgeon can choose the best fitting prosthesis to match the resected anatomy of distal femur 72. Advantageously, the surgeon can intraoperatively adjust the fit of a prosthesis 70 while simultaneously maintaining the most bone-conserving approach because the surgeon is not required to further resect distal femur 72 to provide the best fit. The surgeon can instead select a prosthesis 70 which will provide the greatest probability of a smooth transition with the patella when transitioning between flexion and extension. In an exemplary embodiment, the distal thicknesses of prostheses 70a, 70b, and 70c may differ by approximately 1 to 2 mm, for example. In alternative embodiments, the distal thicknesses may differ by smaller or larger increments than 1 to 2 mm. In one embodiment, a plurality of augments of varying thicknesses may be utilized with prostheses 70a, 70b, and 70c to further enhance the transition and fit of prosthesis 70 and to accommodate for potential dysplastic conditions on distal femur 72.

Figure 4:
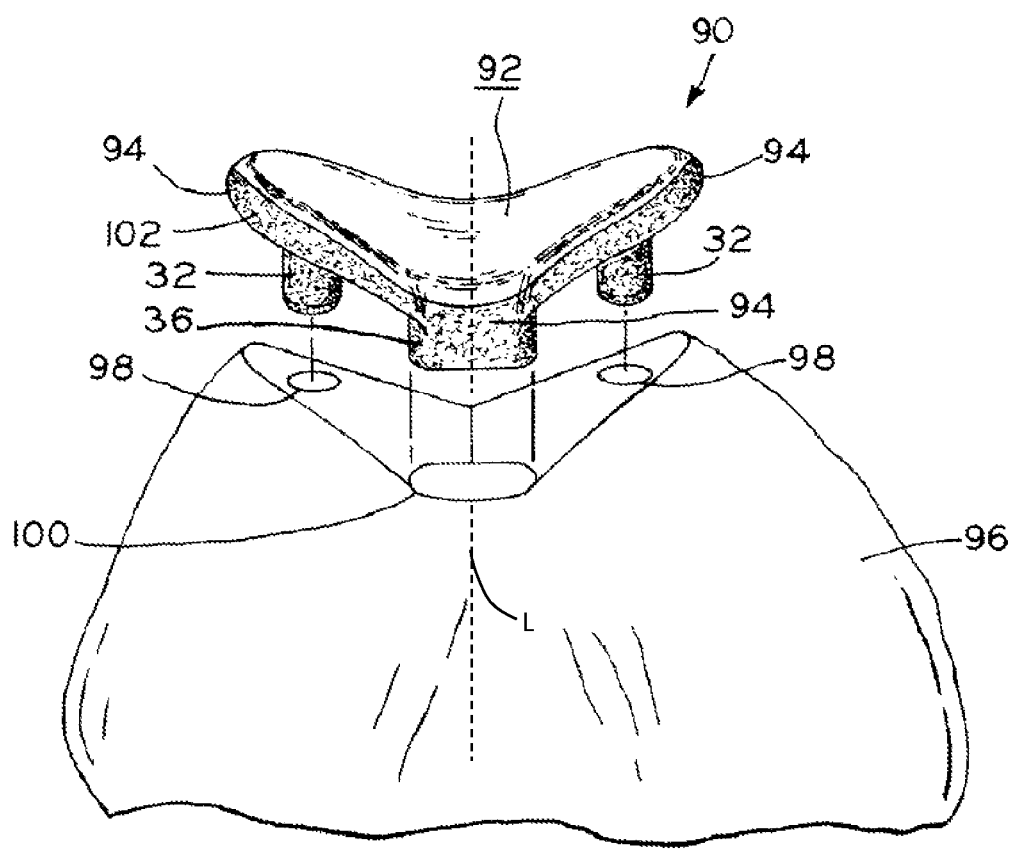
FIG. 4 is an exploded perspective view of an exemplary femoral trochlea prosthesis according to still another embodiment of the present disclosure.

Referring to FIG. 4, femoral trochlea prosthesis 90 may be implantable in distal femur 96. Prosthesis 90 may include a plurality of bone pegs 32 and distal tail 36, as described above with reference to FIGS. 1A, 1B, and 1C. Distal femur 96 may include resected portions 98 and 100 for receipt of bone pegs 32 and distal tail 36, respectively. Prosthesis 90 includes articulating surface 92 which defines perimeter 94 therearound. Porous medium 102 may be positioned near perimeter 94 and on any other surfaces of prosthesis 90 which are proximate to bone or cartilage after implantation of prosthesis 90, e.g., distal tail 36, bone pegs 32, and the nonarticulating surface of prosthesis 90. Porous medium 102 may be formed as an inlay around perimeter 94 and may include cartilage and/or bone ingrowth/regrowth media or scaffolding. Porous medium 102 may promote cartilage and/or bone ingrowth for long-term stability of adjacent cartilage and bone at intersections between the cartilage and/or bone and prosthesis 90. Medium 102 may be formed as, but not limited to, materials such as collagen scaffold, as a bioresorbable beta-chitin sponge, as a polymer scaffold, as an open-cell porous metal such as a material made using Trabecular Metal™ technology, available from Zimmer, Inc. of Warsaw, Ind., as fibrous metal, or as material made using Cancellous-Structured Titanium™ (CSTi™) technology, available from Zimmer, Inc. of Warsaw, Ind., for example.

Although described in FIG. 4 and above as a femoral trochlea prosthesis, prosthesis 90 may be any orthopedic implant, such as a patella, tibial component, a shoulder component, or a hip component, for example, which may include porous medium 102 positioned near a perimeter 94 thereof.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method of surgically repairing a distal femur of a knee joint comprising the steps of:
   providing or obtaining a femoral trochlea prosthesis comprising:
      an anterior articulating surface;
      an anterior non-articulating surface opposite the anterior articulating surface;
      a distal articulating surface having a posterior-most end;
      a distal non-articulating surface opposite the distal articulating surface and oriented at an angle relative to the anterior non-articulating surface; and
      a fixation support that extends from a base coupled to the distal non-articulating surface to a tip opposite the base, the fixation support oriented at an angle relative to the distal non-articulating surface;
   resecting an anterior surface of the distal femur;
   positioning the distal non-articulating surface of the prosthesis against a patella-femoral joint of the distal femur; and
   implanting the tip of the fixation support of the prosthesis into a distal end of the distal femur so that the tip of the fixation support of the prosthesis is surrounded by bone of the distal femur, wherein the implanting step comprises positioning the fixation support of the prosthesis at an acute angle relative to the resected anterior surface of the distal femur.

2. The method of claim 1, further comprising:
   drilling a hole into the distal end of the distal femur, wherein the implanting step comprises inserting the tip of the fixation support of the prosthesis into the drilled hole of the distal femur.

3. The method of claim 1, further comprising the step of positioning the posterior-most end of the distal articulating surface of the prosthesis adjacent to a non-resected distal surface of the distal femur.

4. The method of claim 1, further comprising the step of resecting a distal surface of the distal femur, wherein the implanting step comprises positioning the fixation support of the prosthesis at a substantially perpendicular angle relative to the resected distal surface of the distal femur.

5. A method of surgically repairing a distal femur of a knee joint comprising the steps of:
   providing or obtaining a femoral trochlea prosthesis comprising:

an anterior articulating surface;
an anterior non-articulating surface opposite the anterior articulating surface;
a distal articulating surface having a posterior-most end;
a distal non-articulating surface opposite the distal articulating surface and oriented at an angle relative to the anterior non-articulating surface; and
a fixation support that extends from a base coupled to the distal non-articulating surface to a tip opposite the base, the fixation support oriented at an angle relative to the distal non-articulating surface;
resecting an anterior surface of the distal femur;
resecting a distal surface of the distal femur, the resected anterior and distal surfaces forming an obtuse angle therebetween; and
positioning the distal non-articulating surface of the prosthesis against a patella-femoral joint of the distal femur; and
implanting the tip of the fixation support of the prosthesis into a distal end of the distal femur so that the tip of the fixation support of the prosthesis is surrounded by bone of the distal femur.

6. The method of claim 5, further comprising:
drilling a hole into the distal end of the distal femur, wherein the implanting step comprises inserting the tip of the fixation support of the prosthesis into the drilled hole of the distal femur.

7. The method of claim 5, wherein the implanting step comprises positioning the fixation support of the prosthesis at a substantially perpendicular angle relative to the resected distal surface of the distal femur.

8. A method of surgically repairing a distal femur of a knee joint comprising the steps of:
providing or obtaining a femoral trochlea prosthesis comprising:
an anterior articulating surface;
an anterior non-articulating surface opposite the anterior articulating surface;
a distal articulating surface having a posterior-most end;
a first non-articulating surface opposite the distal articulating surface and intersecting at an angle with the anterior non-articulating surface;
a second non-articulating surface opposite the distal articulating surface and intersecting at an angle with the anterior non-articulating surface, the first and second non-articulating surfaces intersecting along a prosthesis line extending in an anterior-posterior direction; and
a fixation support that extends from a base coupled to the first and second non-articulating surfaces to a tip opposite the base, the fixation support being generally centered on the prosthesis line in a posterior region of the first and second non-articulating surfaces and oriented at an angle relative to the first and second non-articulating surfaces;
resecting a first distal surface of the distal femur along a first plane;
resecting a second distal surface of the distal femur along a second plane, the first and second planes that contain the respective first and second resected distal surfaces of the distal femur intersecting along a resection line that extends anteriorly/posteriorly relative to the distal femur;
positioning the first and second non-articulating surfaces of the prosthesis against the first and second resected distal surfaces of the distal femur; and
implanting the tip of the fixation support of the prosthesis into the distal femur.

9. The method of claim 8, wherein the implanting step comprises inserting the tip of the fixation support of the prosthesis proximally into the distal femur such that the tip of the fixation support is surrounded by bone located proximally of the distal non-articulating surface of the prosthesis.

10. The method of claim 8, wherein the prosthesis line is at an obtuse angle relative to the anterior non-articulating surface.

* * * * *